(12) United States Patent
Ramshaw et al.

(10) Patent No.: US 7,112,209 B2
(45) Date of Patent: Sep. 26, 2006

(54) ANATOMICAL WALL REINFORCEMENT FOR THE TREATMENT OF AN INGUINAL HERNIA

(75) Inventors: Bruce Ramshaw, Peachtree City, GA (US); Russell Wilson, Peachtree City, GA (US); Michel Therin, Lyons (FR)

(73) Assignee: Sofradim Production, Trevoux (FR)

( * ) Notice: Subject to any disclaimer, the term of this patent is extended or adjusted under 35 U.S.C. 154(b) by 583 days.

(21) Appl. No.: 10/265,395

(22) Filed: Oct. 7, 2002

(65) Prior Publication Data

US 2004/0068275 A1    Apr. 8, 2004

(51) Int. Cl.
*A61B 17/08* (2006.01)
(52) U.S. Cl. .................... 606/151; 606/213
(58) Field of Classification Search ............ 600/37; 606/151, 153, 213, 215; 623/11.11, 23.64, 623/23.72
See application file for complete search history.

(56) References Cited

U.S. PATENT DOCUMENTS 5,254,133 A * 10/1993 Seid ............................ 606/215
5,697,978 A * 12/1997 Sgro ........................... 623/23.64
6,066,777 A *  5/2000 Benchetrit ................... 424/423

* cited by examiner

*Primary Examiner*—Anhtuan T. Nguyen
*Assistant Examiner*—Tuan V. Nguyen
(74) *Attorney, Agent, or Firm*—Oliff & Berridge, PLC

(57) ABSTRACT

This reinforcement comprises a first piece and a second piece which are assembled with one another, said first piece comprising a longitudinal edge of corrugated shape, level with which said second piece is fixed.

In this reinforcement, said first piece comprises a cutout forming a zone, located at a distance from said longitudinal edge, for the spermatic cord to pass through it, and comprises a flap which is joined to it and is dimensioned so as to extend close to said longitudinal edge and to broadly cover the zone of said first piece extending between said longitudinal edge and said passage zone, this flap being raisable in relation to said first piece in order to engage the spermatic cord between said first piece and itself and being foldable against said first piece in order to hold this cord between this first piece and itself.

9 Claims, 2 Drawing Sheets

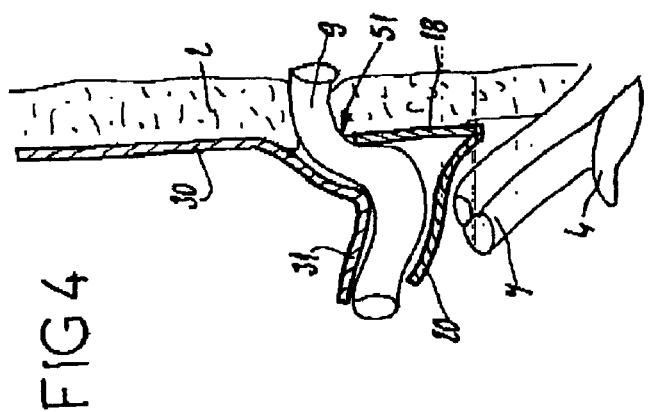
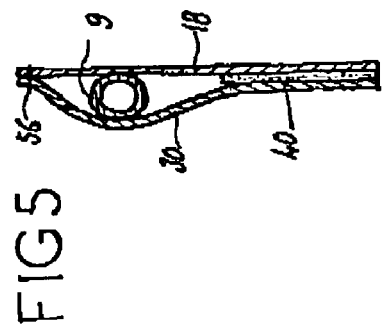
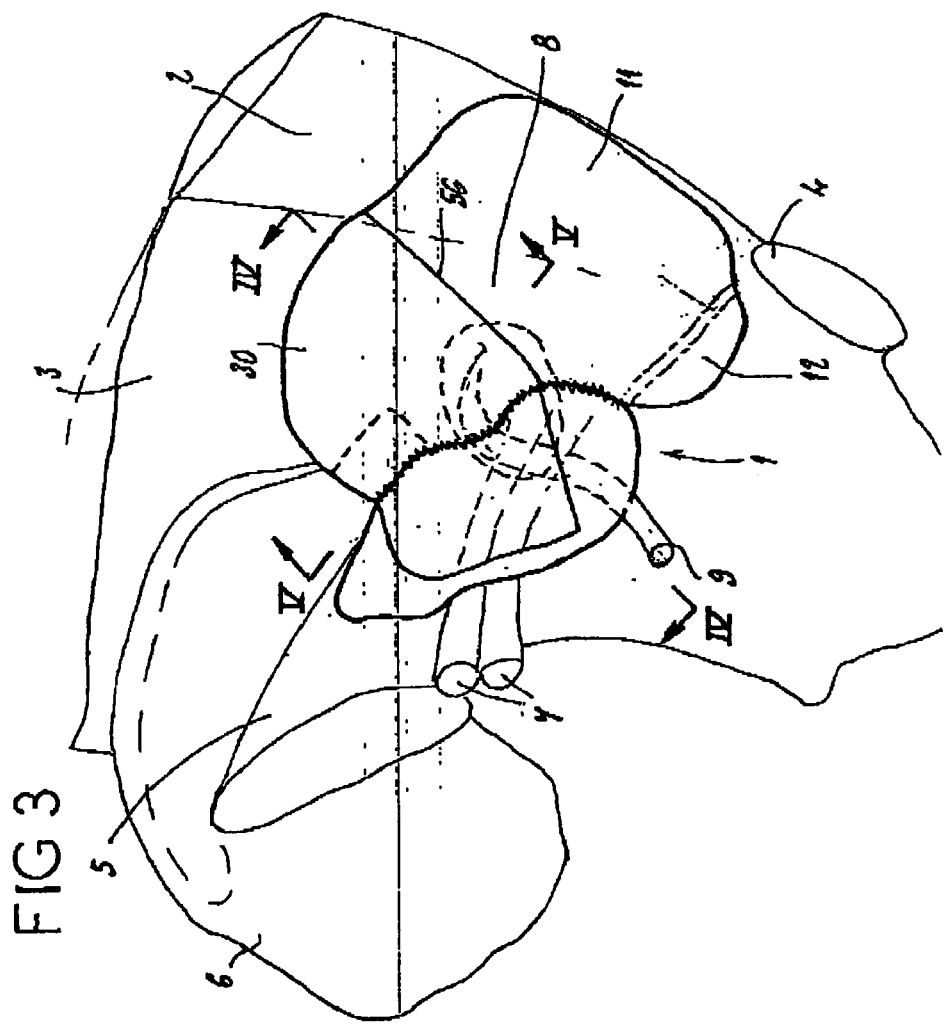

ANATOMICAL WALL REINFORCEMENT FOR THE TREATMENT OF AN INGUINAL HERNIA

BACKGROUND OF THE INVENTION

The present invention relates to an anatomical wall reinforcement for the treatment of an inguinal hernia, in particular by using laparoscopy.

An inguinal hernia results from the passage of the peritoneum, accompanied or not by certain viscera, through the inguinal canal that is taken by the spermatic cord (a hernia which is then referred to as indirect or oblique external) or through the femoral canal that is taken by the iliac vessels (a hernia which is then referred to as femoral), or through a weak zone of the inguinal abdominal wall located medially in relation to the epigastric vessels (a hernia which is then referred to as direct).

For the treatment of such a hernia, it is known to use an anatomical wall reinforcement formed by one or more porous prosthetic pieces made of a biocompatible openworked material, this reinforcement being placed around the internal orifice of the inguinal canal, between the peritoneum and the abdominal muscles.

A known "anatomical" reinforcement comprises a first piece and a second piece which are assembled with one another.

The first piece has an inverted "L" shape comprising a main part intended to rest against the muscle wall, in particular the rectus and transverse muscles, and a secondary part, which is smaller in area, intended to cover the upper end of the pubic bone and the Cooper's ligament. The longitudinal edge of the main part, from which said secondary part projects, has a more or less corrugated shape suited to that of the lower inguinal structures, namely in particular the spermatic and iliac vessels and the psoas muscle.

The second piece is assembled with the first piece along a part or all of this longitudinal edge and the side edge of said secondary part consecutive to this longitudinal edge, and is intended to match the overall shape of said lower inguinal structures, that is to say the iliac vessels and the psoas muscle laterally.

In certain surgical techniques, the spermatic cord needs to pass through this reinforcement and, in order to permit this passage, an existing reinforcement comprises a hole formed in said first piece and a cutout joining this hole to a peripheral edge of this first piece; this cutout may be bounded by two flaps that overlap. When said second piece is joined to said first piece over only a part of said longitudinal edge, the spermatic cord can be engaged between said first piece and said second piece until it occupies a notch formed in said first piece or in said second piece, or in both of these pieces.

These holes or notches entail cutting the openworked material forming one and/or other of said pieces, so that they have the drawback of forming a relatively loose zone around the spermatic cord, and therefore around the internal orifice of the inguinal channel. This leads to limited reinforcement of the abdominal wall at this position, which may make recurrence of the hernia possible.

Furthermore, these holes or notches require that the reinforcement be fitted in a specific position, defined by the position of the spermatic cord, which may cause difficulties for carrying out this fitting.

The present invention aims to overcome these drawbacks.

It is therefore an object of the invention to provide an anatomical wall reinforcement for the treatment of an inguinal hernia which makes it possible to effectively prevent any recurrence of the hernia, particularly around the spermatic cord in the case of split prostheses.

It is also an object of the invention to provide a reinforcement which does not require specific positioning of this reinforcement in order to allow the spermatic cord to pass through this reinforcement.

It is additionally an object of the invention to make it easier to engage the spermatic cord through the reinforcement.

SUMMARY OF THE INVENTION

The reinforcement according to the invention comprises a first piece and a second piece which are assembled with one another, said first piece having a main part intended to rest against the muscle wall, in particular the rectus and transverse muscles, and a secondary part, which is smaller in area, intended to cover the upper end of the pubic bone and the Cooper's ligament, the longitudinal edge of said main part, from which said secondary part projects, and the side edge of this secondary part consecutive to this longitudinal edge, having a more or less corrugated shape suited to that of the lower inguinal structures, namely in particular the spermatic and iliac vessels and the psoas muscle, said second piece being assembled with said first piece along a part or all of said longitudinal edge and said side edge, and being intended to match the overall shape of said lower inguinal structures.

In this reinforcement, said first piece comprises a cutout forming a zone, located at a distance from said longitudinal edge, for the spermatic cord to pass through it, and comprises a flap which is joined to it and is dimensioned so as to extend close to said longitudinal edge and to broadly cover the zone of said first piece extending between said longitudinal edge and said passage zone, this flap being raisable in relation to said first piece in order to engage the spermatic cord between said first piece and itself and being foldable against said first piece in order to hold this cord between this first piece and itself.

The zones through which the spermatic cord enters through the reinforcement and emerges beyond this reinforcement are hence mutually offset and separated, so that the spermatic cord does not cross the reinforcement along a direct path, substantially perpendicular to said first piece, but along a chicane path. This path is furthermore formed between said first piece, on the one hand, and said flap, on the other hand, and therefore between two thicknesses of material.

This path configuration and these two thicknesses of material eliminate any cutting of an orifice in said first piece, through which the spermatic cord is intended to pass directly, running the risk of forming a more or less loose zone of this first piece around the spermatic cord. In the reinforcement according to invention, conversely, the cord enters the reinforcement while being received against said zone of the first piece extending between said longitudinal edge and said passage zone, and leaves the reinforcement via said passage zone, level with which it is perfectly covered by said flap.

This reinforcement hence makes it possible to perfectly prevent any recurrence of the hernia.

Furthermore, said flap does not define a precise zone for engagement of the spermatic cord through the reinforcement, and therefore does not necessitate specific positioning of this reinforcement in order to permit this passage. This makes it easier to fit the reinforcement, and the flap itself makes it easier to engage the spermatic cord through the reinforcement.

The width of said zone of the first piece extending between said longitudinal edge and said passage zone can range from 0.3 to 1 inch (0.75 to 2.5 cm), depending on the size of the reinforcement.

Advantageously, said cutout may form said passage zone with a shape that is elongate in a direction substantially parallel to the overall longitudinal direction of said longitudinal edge.

This elongate passage zone also makes it possible not to define a specific passage point of the spermatic cord through the reinforcement, and therefore not to dictate a specific position for fitting the reinforcement.

Preferably, said cutout consists of a notch bounded by edges respectively substantially perpendicular and substantially parallel to the overall longitudinal direction of said longitudinal edge.

The flap is preferably joined to said first piece along a line substantially parallel to the overall longitudinal direction of said longitudinal edge, this line being, in particular, a seam line.

Advantageously, the flap has an extension which, when this flap is placed against said first piece, covers said second piece.

This extension contributes to effectively preventing the risk of a recurrence of the hernia.

Advantageously, the flap is held against said first piece by means of a piece of gripping material fixed on said first piece or on said flap, this piece of gripping material comprising spikes capable of being inserted into the fibers of said flap or of said first piece, and capable of hooking these fibers.

This gripping material permits reliable holding of the flap along said first piece.

BRIEF DESCRIPTION OF THE FIGURES

The present invention is now described with reference to the appended drawing, in which:

FIG. 3 is a perspective view of it after installation, the site of installation being represented in a very simplified way;

FIG. 4 is a sectional view of it on the line IV—IV of FIG. 3, and

FIG. 5 is a view of it on the line V—V of FIG. 3.

EXPLANATION OF AN EMBODIMENT OF THE INVENTION

Figure 2:
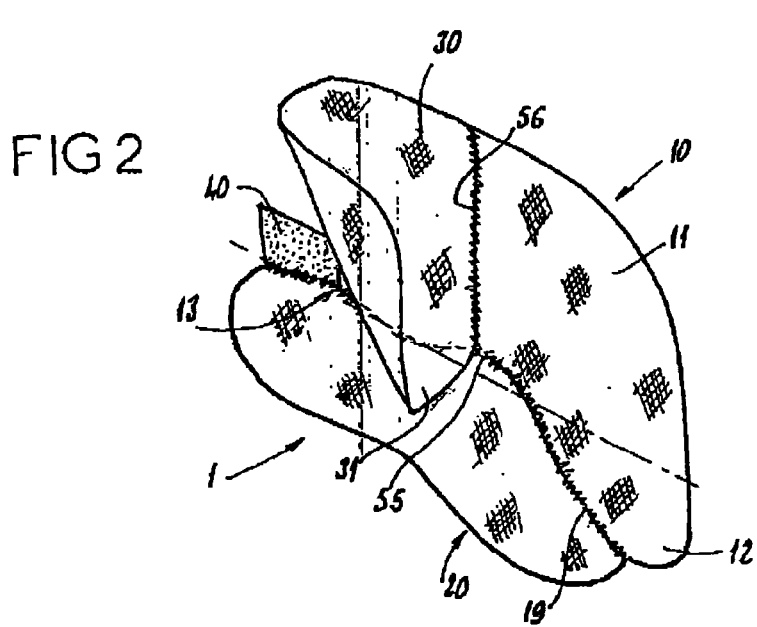
FIG. 2 is a perspective view of this reinforcement.

FIGS. 2 and 3 represent an anatomical wall reinforcement 1 for the treatment of an inguinal hernia. The example which is represented involves a reinforcement for treatment of an inguinal hernia of the left side, a reinforcement with a symmetrical shape being used for treating an inguinal hernia of the right side.

FIG. 3 shows, further to the reinforcement 1, the extraperitoneal inguinal region, seen from the interior of the abdomen toward the outside thereof. It is possible to recognize therein the rectus muscle 2, the transverse muscle 3, the pubic tubercule 4, the psoas muscle 5, the iliac flank 6, the spermatic and iliac vessels 7, the internal orifice 8 of the inguinal canal and the spermatic cord 9. The peritoneum, the fascia transversalis and the Cooper's ligament are not represented, for the sake of clarity of the drawing.

Figure 1:
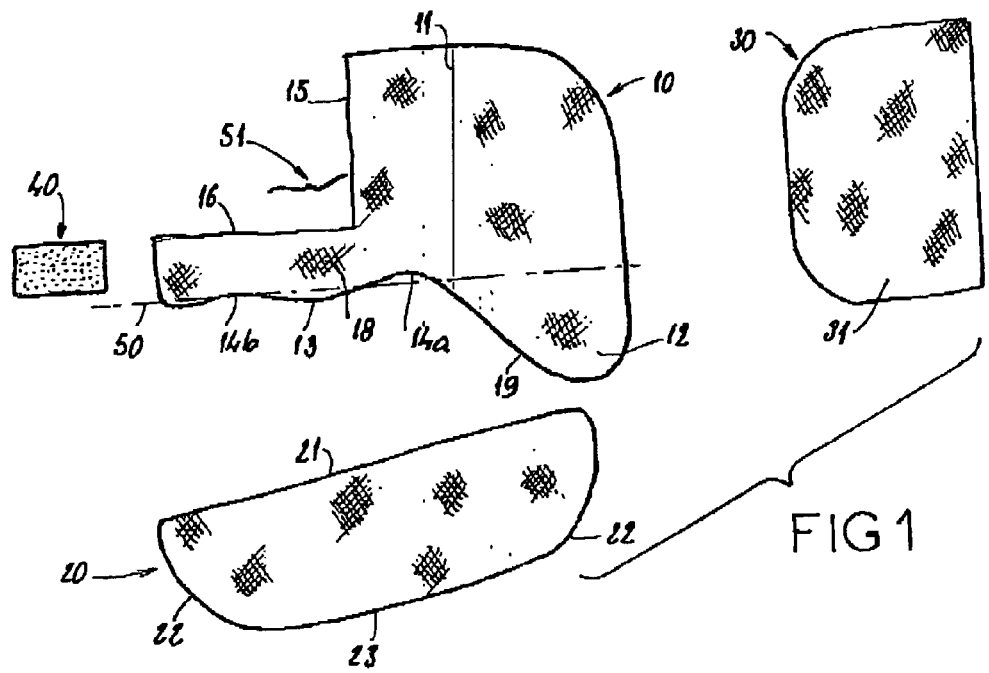
FIG. 1 is an exploded plan view of the various pieces constituting the reinforcement which it concerns.

As shown by FIGS. 1 and 2, the reinforcement 1 comprises a first piece 10, a second piece 20, a flap 30, and a piece 40 of gripping material.

The piece 10 is made of a porous and flexible material that is relatively rigid compared with the material of the piece 20, for example made of a single-thickness fabric of polyester multifilament yarns. It has a main part 11 intended to rest against the muscle wall, in particular the rectus 2 and transverse 3 muscles, and a secondary part 12, which is smaller in area, intended to cover the upper end of the pubic bone and the Cooper's ligament.

The longitudinal edge 13 of the main part 11, from which the secondary part 12 projects, has a corrugated shape defining a hollow 14a close to the part 12, designed to go around the spermatic and iliac vessels 7, and a hollow 14b distant from the part 12, designed to match the shape of the psoas muscle 5.

The piece 10 also comprises a notch bounded by edges 15 and 16 respectively substantially perpendicular and substantially parallel to the overall longitudinal direction 50 of the longitudinal edge 13. These edges 15 and 16 form a zone 51, located at a distance from the longitudinal edge 13 and having a shape that is elongate in a direction substantially parallel to said overall longitudinal direction 50, for the spermatic cord 9 to pass beyond the piece 10. The width of the zone 18 of the piece 10 extending between the longitudinal edge 13 and the edge 16 can range from 0.3 to 1 inch (0.75 to 2.5 cm), depending on the size of the reinforcement 1. The second piece 20 is also made of a porous and flexible material, more supple than the material constituting the piece 10, for example made of a knitted fabric or a fabric of polyester multifilament yarns having a thickness of from 1 to 2 mm.

This piece 20 has a straight longitudinal edge 21, rounded end edges 22 and a longitudinal edge 23 opposite the edge 21 that is substantially straight. As can be seen in FIG. 2, the piece 20 is assembled with the piece 10 along all of the longitudinal edge 13 and the side edge 19 of the secondary part 12 consecutive to this longitudinal edge 13, by a seam 55 made slightly set-back from these edges 13 and 19. The piece 20 hence has a corrugated shape which follows the curvatures of the edge 13 and the edge 19, suited to the shape of the lower anatomical structures of the inguinal space to be treated, which it partially covers.

The flap 30 is made of a porous and flexible material, more supple than the material constituting the piece 10. It may, in particular, be made of the same material as that constituting the piece 20.

This flap 30 is joined to the piece 10 along a seam line 56 substantially parallel to the overall longitudinal direction 50 of the longitudinal edge 13, and it is dimensioned so as to cover the notch formed in the piece 10, the zone 18, and, by a free extension 31 that extends it, the part of the piece 20 that extends facing it.

The piece 40 comprises a woven or knitted base structure and includes gripping spikes capable of being inserted into the structure of the flap 30 and of gripping the yarns and fibers of it.

This piece 40 is dimensioned so as to occupy only a part of the zone 18, and it is fixed to this zone 18 on the longitudinal side of the piece 10 opposite the one on which the part 12 is located, at a distance from the edge 15. It makes it possible to hold the flap 30 flat against the piece 10.

The reinforcement 1 is intended to be fitted in the inguinal space to be treated, in particular via a posterior route by using a laparoscopy technique. This technique, which is well known per se and will not therefore be described in detail, comprises the formation of an extraperitoneal space between the fascia transversalis and the rectus and transverse muscles by blowing air in and separating the peritoneum and the abdominal wall, then fitting one or more working trocars, one of which makes it possible to introduce the reinforcement 1.

After introduction, the latter is deployed in said extraperitoneal space; the part 11 of the piece 10 comes to rest against the rectus and transverse muscles and the part 12 comes to rest against the pubic bone while covering the Cooper's ligament, the lower edge of the part 11 coming to rest against the vessels 7 while going around them, and coming to bear against the psoas muscle 5; for its part, the piece 20 comes to cover these vessels 7 and a part of the psoas muscle 5.

The flap 30 is raised so as to make it possible to engage the spermatic cord 9 along the zone 18, then it is folded against the piece 10 so as to be gripped by the piece 40.

It can be seen in FIG. 4 that, in this folded position of the flap 30, the spermatic cord 9 enters the reinforcement 1 while being received against the zone 18, and leaves the reinforcement 1 via said passage zone 51, beyond the edge 16. The zones via which the spermatic cord 9 enters through the reinforcement 1 and emerges beyond this reinforcement are hence mutually offset and separated, so that the spermatic cord 9 crosses the reinforcement 1 along a chicane path.

This path is formed between the zone 18, on one hand, and the flap 30, on the other hand, which perfectly covers the spermatic cord 9, in particular level with the passage zone 51.

The reinforcement 1 hence makes it possible to perfectly prevent any recurrence of the hernia.

Furthermore, as can be seen in FIG. 5, the passage zone 51 and the flap 30 do not define a precise zone for engagement of the spermatic cord 9 through the reinforcement 1. This zone 51 and this flap 30 do not therefore necessitate specific positioning of the reinforcement 1 at the installation site, and they make it possible to position the medial edge of the reinforcement 1 beyond the median line, if necessary. This makes it easier to fit the reinforcement 1, and the flap 30 itself makes it easier to engage the spermatic cord 9 through the reinforcement 1.

As demonstrated above, the invention provides decisive improvements to the similar reinforcements of the prior art.

It is self-evident that the invention is not limited to the embodiment described above by way of example, but, on the contrary, it encompasses all the alternative embodiments of it which fall within the scope of protection defined by the appended claims.

The invention claimed is:

1. An anatomical wall reinforcement for the treatment of an inguinal hernia, comprising a first piece and a second piece which are assembled with one another, said first piece having a main part resting against the muscle wall, and a secondary part, which is smaller in area, substantially covering an upper end of a pubic bone and the Cooper's ligament, a longitudinal edge of said main part, from which said secondary part projects, having a relatively corrugated shape suited to that of lower inguinal structures, said second piece being assembled with said first piece along a part or all of said longitudinal edge and the side edge of said secondary part consecutive to this longitudinal edge, and substantially matching the overall shape of said lower inguinal structures, wherein said first piece comprises a cutout forming a passage zone, located at a distance from said longitudinal edge, for a spermatic cord to pass therethrough, and a flap which is joined thereto and is dimensioned so as to extend close to said longitudinal edge and to broadly cover the passage zone of said first piece extending between said longitudinal edge and said passage zone, the flap being raisable in relation to said first piece to engage the spermatic cord between said first piece and the flap and being foldable against said first piece to hold the spermatic cord between said first piece and the flap, and wherein the width of said passage zone of the first piece extending between said longitudinal edge and said passage zone ranges from 0.3 to 1 inch (0.75 to 2.5 cm), depending on the size of the reinforcement.

2. The anatomical wall reinforcement as claimed in claim 1, in which said cutout forms said passage zone with a shape that is elongate in a direction substantially parallel to the overall longitudinal direction of said longitudinal edge.

3. The anatomical wall reinforcement as claimed in claim 1, in which said cutout consists of a notch bounded by edges respectively substantially perpendicular and substantially parallel to the overall longitudinal direction of said longitudinal edge.

4. The anatomical wall reinforcement as claimed in claim 1, in which the flap is joined to said first piece along a line substantially perpendicular to the overall longitudinal direction of said longitudinal edge.

5. The anatomical wall reinforcement as claimed in claim 4, in which said line is a seam line.

6. The anatomical wall reinforcement as claimed in claim 1, in which the flap has an extension which, when this flap is placed against said first piece, covers said second piece.

7. The anatomical wall reinforcement as claimed in claim 1, in which the flap is held against said first piece by a piece of gripping material fixed on said first piece or on said flap, the piece of gripping material comprising spikes capable of being inserted into the fibers of said flap or of said first piece, and capable of hooking the fibers.

8. The anatomical wall reinforcement as claimed in claim 1, wherein the main part rests against rectus and transverse muscles.

9. The anatomical wall reinforcement as claimed in claim 1, wherein the longitudinal edge of said main part has the corrugated shape suited to that of spermatic and iliac vessels and psoas muscle.

* * * * *